United States Patent [19]

Bogden

[11] Patent Number: 5,595,973
[45] Date of Patent: Jan. 21, 1997

[54] PROTECTION OF HEMOPOIETIC CELLS DURING CHEMOTHERAPY OR RADIOTHERAPY

[75] Inventor: Arthur E. Bogden, Hopedale, Mass.

[73] Assignee: Biomeasure Incorporated, Milford, Mass.

[21] Appl. No.: 304,724

[22] Filed: Sep. 12, 1994

[51] Int. Cl.$^6$ .......................... A61K 38/07; A61K 38/00
[52] U.S. Cl. ................................ 514/18; 424/85.2; 514/2; 514/21
[58] Field of Search ................................ 424/85.1, 85.2, 424/85.3, 85.4; 514/2, 12, 18, 21

[56] References Cited

U.S. PATENT DOCUMENTS 5,114,926  5/1992  Frindel et al. ............................ 514/18

OTHER PUBLICATIONS

Castelli et al., "Protective, Restorative, and Therapeutic Properties of Recombinant Human IL–1 in Rodent Models", The Journal of Immunology 140:3830–3837, 1988.
Fibbe, et al., "A Single Low Dose of Human Recombinant Interleukin 1 Accelerates the Recovery of Neutrophils in Mice with Cyclophosphamide–induced Neutropenia", Experimental Hematology 17:805–808, 1989.
Futami et al., "Chemoprotective Effects of Recombinant Human IL–1α In Cyclophosphamide–Treated Normal and Tumor–Bearing Mice", The Journal of Immunology 145:4121–4130, 1990.
Gianni et al., "Recombinant Human Granulocyte–Macrophage Colony–Stimulating Factor Reduces Hematologic Toxicity and Widens Clinical Applicability of . . . ", Journal of Clinical Oncology 8:768–778, 1990.
Guigon et al., "Convenient Source of CFU–s Inhibitors: The Fetal Calf Liver", Cell Tissue Kinet 17:49–55, 1984.
Guigon et al., "Effects of CFU–S Inhibitors on Murine Bone Marrow During ARA–C Treatment—1. Effects On Stem Cells", Leukemia Research 4:385–391, 1980.
Lenfant et al., "Inhibitor of Hematopoietic Pluripotent Stem Cell Proliferation: Purification and Determination of its Structure", Proc. Nat. Acad. Sci. USA 86:779–782, 1989.
Moore et al., "Synergy of Interleukin 1 and Granulocyte colony–Stimulating Factor: In vivo Stimulation of Stem–Cell Recovery and Hematopoietic Regeneration . . . ", Proc. Natl. Acad. Sci. USA 84:7134–7138, 1987.
Neta et al., "Interleukin 1 is a Radioprotector", The Journal of Immunology 136:2483–2485, 1986.
Oppenheim et al., "Interleukin–1 Enhances Survival of Lethally Irradiated Mice Treated With Allogeneic Bone Marrow Cells", Blood 74:2257–2263, 1989.
Schuening et al., "Effect of Recombinant Human Granulocyte Colony–Stimulating Factor on Hematopoiesis of Normal Dogs & on Hematopoietic Recovery After Otherwise Lethal Total Body . . . ", Blood 74:1308–1313, 1989.
Steward et al., "Clinical Applications of Myeloid Colony Stimulating Factors", Cancer Treatment Reviews 17:77–87, 1990.

Tanikawa et al., "Effects of Recombinant Granulocyte Colony–Stimulating Factor (rG–CSF) and Recombinant Granulocyte–Macrophage Colony–Stimulating . . . ", Exp. Hemotol 17:883–888, 1989.

Thierry et al., "Synthesis and Activity of NAcSerAspLysPro Analogues on Cellular Interactions Between T–Cell and Erythrocytes in Rosette Formation", J. Med. Chem. 33:2122–2127, 1990.

Till et al., "A Direct Measurement of the Radiation Sensitivity of Normal Mouse Bone Marrow Cells", Radiation Research 14:213–222, 1961.

Tubiana et al., "Ways of Minimizing Hematopoietic Damage Induced by Radiation and Cytostatic Drugs –The Possible Role of Inhibitors", Radiotherapy and Oncology 29:1–17, 1993.

Wdzieczak–Bakala et al., "Further Purification of a CFU–S Inhibitor: In vivo Effects After Cytosine Arabinoside Treatment", Biomedicine & Pharmacotherapy 37:467–471, 1983.

Welte et al., "Recombinant Human Granulocyte Colony–Stimulating Factor . . . ", J. Exp. Med. 165:941–948, 1987.

Robinson et al., "The Molecular Specificity of Action of the Tetrapeptide Acetyl–N–Ser–Asp–Lys–Pro (AcSDKP) in the Control of Hematopoietic Stem Cell Proliferation", Stem Cells 11:422–427, 1993.

Paukovits et al., "Pre–CFU–S Quiescence and Stem Cell Exhaustion After Cytostatic Drug Treatment: Protective Effects of the Inhibitory Peptide pGlu–Glu–Asp–Cys–Lys (pEEDCK)", Blood 81:1755–1761, 1993.

*Primary Examiner*—Ponnathapura Achutamurthy
*Attorney, Agent, or Firm*—Fish & Richardson P.C.; William E. McGowan

[57] ABSTRACT

A method of promoting regeneration of hemopoietic cells in a subject undergoing chemotherapy or radiotherapy, which method includes the steps of (i) administering to the subject a first amount of a hemopoiesis inhibitory factor, the first amount being effective to reduce the proliferation of hemopoietic cells during the chemotherapy or radiotherapy; and (ii) after the chemotherapy or radiotherapy, administering to the subject a second amount of a hemopoiesis growth factor, the second amount being effective to stimulate the proliferation of hemopoietic cells.

18 Claims, 3 Drawing Sheets

5,595,973

PROTECTION OF HEMOPOIETIC CELLS DURING CHEMOTHERAPY OR RADIOTHERAPY

BACKGROUND OF THE INVENTION

Acute and chronic bone marrow toxicities are the major limiting factors in the treatment of cancer. They are both related to two causes. The first is a decrease in the number of hemopoietic cells (e.g., pluripotent stem cells and other progenitor cells) caused by both a lethal effect of cytotoxic agents or radiation on these cells and by differentiation of stem cells provoked by a feed-back mechanism induced by the depletion of more mature marrow compartments. The second cause is a reduction in self-renewal capacity of stem cells, which is also related to both direct (mutation) and indirect (aging of stem cell population) effects. Stimulators and inhibitors of bone marrow kinetics play a prominent role in the induction of damage and recovery patterns (Tubiana, M., et al., Radiotherapy and Oncology 29:1, 1993).

Acute myelosuppression as a consequence of cytotoxic chemotherapy is well recognized as a dose-limiting factor in cancer treatment. Although other normal tissues may be adversely affected, bone marrow is particularly sensitive to the proliferation-specific treatment such as chemotherapy or radiotherapy.

Self-renewing, pluripotent hemopoietic stem cells, as measured by spleen colony-forming units (CFU-S), are responsible for generation of the hemopoietic system (Till, J. E., et al., Radiat. Res. 14:213, 1961). Such stem cells are mainly quiescent, and renewal of mature cells is provided by the partially differentiated, lineage-committed hemopoietic progenitors. At this stage, the stem cells are relatively invulnerable to chemotherapy and radiotherapy that affects only those cells that are already in proliferation or about to begin proliferation. The stem cell compartment of the bone marrow that guarantees a sufficient supply of cells bound for differentiation, though mainly quiescent, still has approximately 10% of its cellular component in some state of mitosis (Lajtha, L. G., In Stem Cells, Ed: C. S. Potten, Churchill Livingstone, Edinburgh, 1–11, 1983). During chemotherapy or radiotherapy, the first treatment kills proliferating malignant or infected cells as well as proliferating hemopoietic cells in the bone marrow, but has no effect on the quiescent CFU-S. Therefore, the given situation before treatment is favorable for therapy as the stem cell population is relatively resistant. Subsequent treatment, however, will cause severe damage to the stem cell population, since they will have begun compensatory proliferation.

SUMMARY OF THE INVENTION

The present invention relates to a method of promoting regeneration of hemopoietic cells in a subject undergoing chemotherapy or radiotherapy.

More specifically, the method of this invention includes the steps of (i) administering to the subject a first amount of a hemopoiesis inhibitory factor, the first amount being effective to reduce the proliferation of hemopoietic cells during the chemotherapy or radiotherapy; and (ii) after the chemotherapy or radiotherapy, administering to the subject a second amount of a hemopoiesis growth factor, the second amount being effective to stimulate the proliferation of hemopoietic cells. As will be further discussed below, by "chemotherapy" is meant a process of killing proliferating cells using a cytotoxic agent. The phrase "during the chemotherapy" above refers to the period in which the effect of the administered cytotoxic agent lasts. On the other hand, the phrase "after the chemotherapy" above is meant to cover all situations in which a hemopoiesis growth factor is administered after the administration of a cytotoxic agent regardless of any prior administration of the same or another hemopoiesis growth factor and also regardless of the persistence of the effect of the administered cytotoxic agent.

Examples of a hemopoiesis inhibitory factor which can be used to practice the above method include, but are not limited to, a transforming growth factor, an interferon, a macrophage inflammatory protein, a tumor necrosis factor, pEEDCK (i.e., pyroGlu-Glu-Asp-Cys-Lys), (SEQ ID NO:1) AcSDKP (i.e., N-Acetyl-Ser-Asp-Lys-Pro), (SEQ ID NO:2) and an agonist of any of the above factors. Using a transforming growth factor as an example, by "agonist" is meant an analog (with one or more modifications) or a fragment of that factor with the same desired activity, i.e., inhibiting the proliferation of hemopoietic cells. Note that a hemopoiesis inhibitory factor can be a non-peptide compound.

Examples of a hemopoiesis growth factor which can be used to practice the above method include, but are not limited to, cytokines or agonists thereof, such as natural, synthetic or modified interleukins (e.g., IL-1, IL-3, IL-6, IL-11, or its agonist), G-CSF (i.e., granulocyte colony-stimulating factor), GM-CSF (i.e., granulocyte/macrophage-colony stimulating factor), erythropoietin, stem cell factor, and leukemia inhibitory factor.

In one embodiment of this method, the subject is undergoing chemotherapy with a cytotoxic agent. By "cytotoxic agent" is meant an agent which kills proliferating cells, e.g., tumor cells, virally infected cells, or hemopoietic cells. Examples of a cytotoxic agent which can be used to practice the above method include, but are not limited to, cyclophosphamide, taxol, 5-fluorouracil, adriamycin, cisplatinum, methotrexate, cytosine arabinoside, mitomycin C, prednisone, vindesine, carboplatinum, vincristine, and an agonist of any of the above compounds. A cytotoxic agent can also be an antiviral agent, e.g., AZT (i.e., 3'-azido-3'-deoxythymidine). In another embodiment of this method, the subject is undergoing radiotherapy. Note that the terms "chemotherapy" and "radiotherapy" used herein refer to the process of killing proliferating cells by administration of a cytotoxic agent or by irradiation.

When the method of this invention is applied to chemotherapy, a hemopoiesis inhibitory factor can be administered prior to, during, or subsequent to the chemotherapy (i.e., prior to, during, or subsequent to the administration of a cytotoxic agent). In any event, it is preferred that a hemopoiesis growth factor be administered subsequent to the administration of a hemopoiesis inhibitory factor. When the method of this invention is applied to radiotherapy, a hemopoiesis inhibitory factor can be administered prior to or during the radiotherapy (i.e., prior to or during the irradiation). Note that the timing of when to administer a hemopoiesis inhibitory factor depends on the half life of that factor, the duration of its inhibitory activity, the administration route, etc., as well as the conditions of the chemotherapy or radiotherapy (e.g., the half life of the cytotoxic agent which is used in chemotherapy).

The effective amount of the hemopoiesis inhibitory factor or growth factor used to practice the present invention varies depending upon the manner of administration, the age and the body weight of the subject, and the condition of the subject to be treated. Ultimately, it will be decided by the attending veterinarian or physician. Any such amount of the inhibitory or growth factor as determined by the attending veterinarian or physician is referred to herein as "effective amount".

Also note that the hemopoiesis inhibitory or growth factor may be administered by any route appropriate to the condition being treated. Preferably, it is injected into the bloodstream of the subject being treated. However, it will be readily appreciated by those skilled in the art that the route, such as intravenous, subcutaneous, intramuscular, intraperitoneal, nasal, oral, etc., will vary with the condition being treated and the activity of the factor being used. Note that continuous administration using a subcutaneous infusion pump may be desirable when the factor to be used has a rather short half life or lacks long-lasting activity. Conversely, single or intermittent administration is acceptable or even preferable when the factor to be used has a long half life or long-lasting activity.

The inhibitory or growth factor may be conveniently be presented as an ingredient of a pharmaceutical composition in unit dosage form according to any of the methods well known in the art of pharmacy. All methods include the step of bringing the active ingredient(s) into association with the carrier which constitutes one or more accessory ingredients. In general, the formulations for tablets or powders are prepared by uniformly and intimately blending the active ingredient with finely divided solid carriers, and then, if necessary as in the case of tablets, forming the product into the desired shape and size.

Other features and advantages of the present invention will be apparent from the following drawings and description of the preferred embodiments, and also from the appending claims.

BRIEF DESCRIPTION OF THE DRAWINGS

The drawings are first briefly described.

DESCRIPTION OF THE PREFERRED EMBODIMENTS

Figure 1:
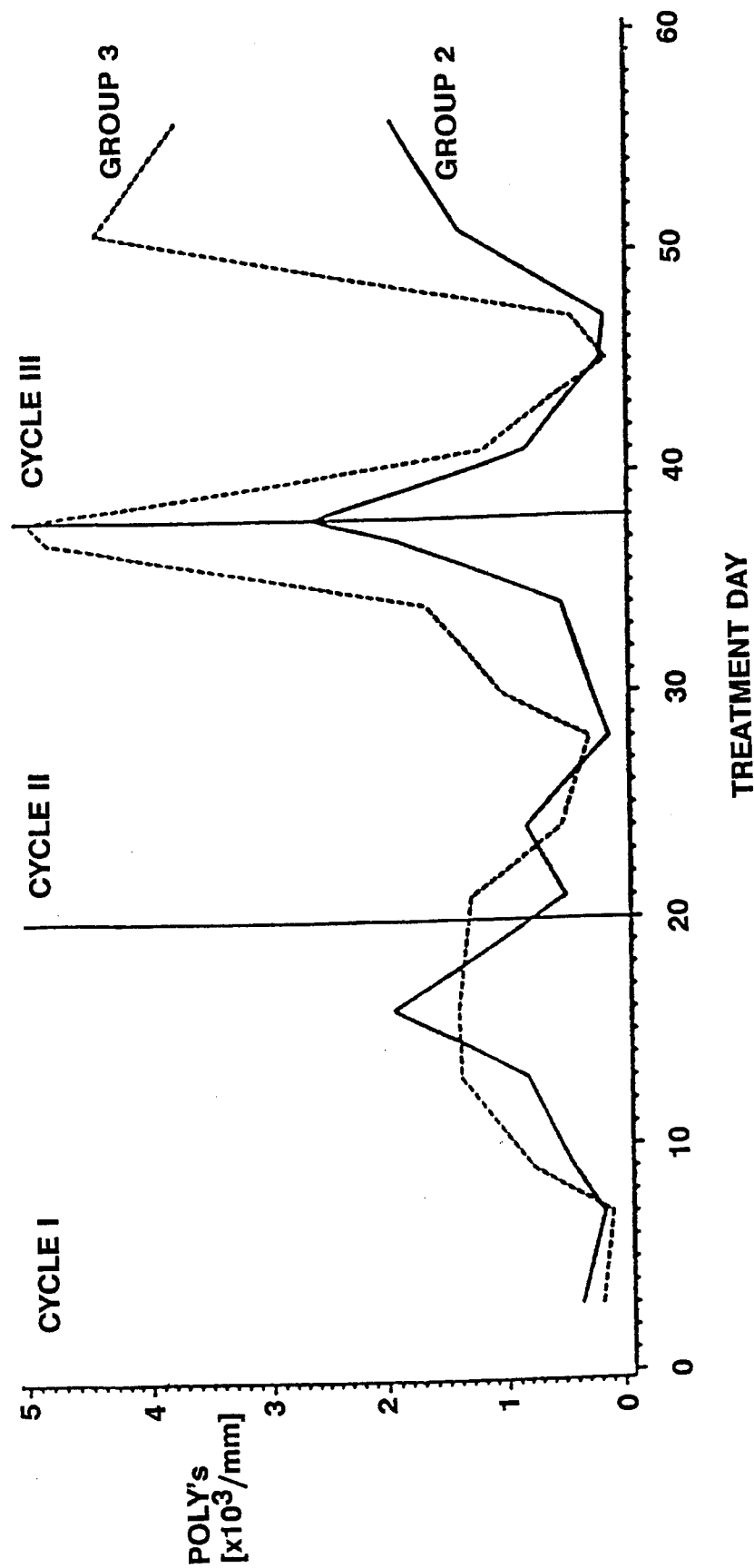
FIG. 1 is a graph showing promotion of regeneration of polymorphonuclear cells during chemotherapy by a method which is an embodiment of this invention.

The hemopoiesis inhibitory factor used to practice this invention is a compound capable of inhibiting the proliferation of hemopoietic cells, e.g., AcSDKP or pEEDCK, or an analog or fragment thereof. Suitable analogs of AcSDKP are described in Theirry et al., J. Med. Chem. 33:2122, 1990; and Robinson et al., Stem Cells, 11:422, 1993, both of which are hereby incorporated by reference. For pEEDCK, see Pavkovits et al., Blood, 81:1755, 1993, which is also incorporated herein by reference. Examples of other hemopoiesis inhibitory factors include macrophage inflammatory protein (e.g., MIP-1α), an interferon (e.g., IFN-δ), a tumor necrosis factor (e.g., TNF-α), and a transforming growth factor (e.g., TGF-β). E.g., see Moore, M., Clinical Implication of Positive and Negative Hemopoietic Stem Cell Regulators; Blood, 78(1):1, 1991, incorporated herein by reference.

On the other hand, the hemopoiesis growth factor which can be used to practice this invention is a compound capable of stimulating the proliferation of hemopoietic cells, such as cytokines. Preferred cytokines include interleukins, GM-CSF, and G-CSF. E.g., see R. Van Furth (ed.), Hemopoietic Growth Factors and Mononuclear Phagocytes (Karges 1993), which is hereby incorporated by reference. Also see the Moore, M. article cited in the preceding paragraph.

Interleukin-1 (IL-1) has shown dramatic hemopoietic protective and restorative effects against lethal doses of irradiation either alone (Neta, R. et al., J. Immunol. 136:2483, 1986) or in concert with bone marrow transfer (Oppenheim, J. J., et al., Blood 74:2257, 1989), and against chemotherapeutic drugs such as cyclophosphamide (Castelli, M. P., et al., J. Immunol. 140:3830, 1988; Futami, H., et al., J. Immunol. 145:4121, 1990; Fibbe, W. E., et al., Exp. Hematol. 17:805, 1989). GM-CSF and G-CSF have also been found to have marked restorative effects after irradiation (Tanikawa, S., et al., Exp. Hematol. 17:883, 1989; Schuening, F. G., et al., Blood 74:1308, 1989) or treatment with chemotherapeutic drugs both in preclinical models (Moore, M. A. S., et al., Proc. Natl. Acad. Sci. USA 84:7134, 1987; Welte, K., et al., J. Exp. Med. 165:941, 1987), as well as in human trials (Steward, W. P., et al., Cancer Treat. Rev. 17:77, 1990; Gianni, A. M., et al., J. Clin. Oncol. 8:768, 1990). All of the references cited in this paragraph are hereby incorporated by reference.

When the method of this invention is applied to chemotherapy, the cytotoxic agent which can be used include cyclophosphamide, taxol, 5-fluorouracil, adriamycin, cisplatinum, methotrexate, cytosine arabinoside, mitomycin C, prednisone, vindesine, carbaplatinum, and vincristine. The cytotoxic agent can also be an antiviral compound which is capable of destroying proliferating cells. For a general discussion of cytotoxic agents used in chemotherapy, see Sathe, M. et al., Cancer Chemotherapeutic Agents: Handbook of Clinical Data (1978), hereby incorporated by reference.

The method of this invention can also be applied to radiotherapy, which may comprise of either ionizing waves or particles. Examples of ionizing waves include x-rays and gamma rays. Examples of ionizing particles include alpha rays, beta rays, neutrons, electrons, and protons. Radiotherapy may be administered externally or internally. Examples of external radiotherapy include x-ray units, gamma ray units, electron beams, and neutron beams. Internal radiotherapy includes both sealed and unsealed sources. Examples of sealed sources include cobalt beam units, caesium beam units, strontium applicators, yttrium rods or pellets, gold grains, or radium, cobalt or caesium needles or tubes. Examples of unsealed sources include iodine, phosphorous, gold, and yttrium. See Walter, J., Cancer and Radiotherapy (Churchill Livingstone 1977); Ed. N.J. McNally, The Scientific Basis of Modern Radiotherapy (British Institute of Radiology 1989); and Franz Buschke and Robert G. Parker, Radiation Therapy in Cancer Management (Grove & Stratton 1972).

In preferred embodiments of this invention, the subject undergoes repeated cycles of treatment according to the method of this invention. Preferably, a subsequent cycle commences only after the administration of the hemopoiesis growth factor has been terminated and the subject's blood cell counts (e.g., white blood cell count) have returned to a therapeutically acceptable level (as determined by the attending veterinarian or physician), permitting the repeated chemotherapy or radiotherapy For obvious reasons, the method of this invention can also be applied to treatment in which radiotherapy and chemotherapy are performed in conjunction.

In chemotherapy, it is desirable that the hemopoiesis growth factor be administered only 1–7 days (preferably, 1–5 days; or more preferably, 2–3 days) after the administration of both the hemopoiesis inhibitory factor and the cytotoxic agent has been terminated. By the same token, in radiotherapy, it is preferred that the hemopoiesis growth factor be administered only after the irradiation has been completed.

Without further elaboration, it is believed that one skilled in the art can, based on the description herein, utilize the present invention to its fullest extent. The following specific example is, therefore, to be construed as merely illustrative, and not limitative of the remainder of the disclosure in any way whatsoever.

In each group, the animals were subjected to a sequence of three cycles of chemotherapy, i.e., Cycle I (Days 0–20), Cycle II (Days 21–37), and Cycle III (Days 38–56). The experimental protocol is summarized in Table 1. Note that animals in each group were sacrificed on specific days for collection of blood samples, eliminating the artifact that may have been induced by intensive repetitive bleedings of the same animals.

AcSDKP, which was prepared by a process described in PCT Application WO 93/25571 (hereby incorporated by reference), can also be obtained as SERASPENIDE™ from Sigma Chemical Co., St. Louis, Mo. Ara-C was purchased from Sigma Chemical Co., and GM-CSF was procured from Immunix Research and Development Corp., Seattle, Wash.

TABLE 1

| GROUP NUMBER | NO. OF MICE | TREATMENT/DAY | DOSE | BLOOD COLLECTION DAY |
|---|---|---|---|---|
| Baseline | 15 | None | 0 | Pretreatment on Day 0 |
| 1 | 136 | Ara-C/Days 0–6, 21–27, 38–44 | 40 to 42 mg/kg/inj (q.d.) | 8 mice on each of Days 3, 7, 9, 13, 16, 21, 24, 28, 30, 34, 37, 38, 41, 45, 47, 51, 56 |
| 2 | 136 | GM-CSF/Days 9–12, 30–33, 47–50 | 300 ng/inj (b.i.d.) | 8 mice on each of Days 3, 7, 9, 13, 16, 21, 24, 28, 30, 34, 37, 38, 41, 45, 47, 51, 56 |
| | | Ara-C/Days 0–6, 21–27, 38–44 | 40 to 42 mg/kg/inj (q.d.) | |
| 3 | 136 | AcSDKP/Days 0–7, 21–28, 38–45 | 100 ng/1.0 μL/hr (continuous) | 8 mice on each of Days 3, 7, 9, 13, 16, 21, 24, 28, 30, 34, 37, 38, 41, 45, 47, 51, 56 |
| | | GM-CSF/Days 9–12, 30–33, 47–50 | 300 ng/inj (b.i.d.) | |
| | | Ara-C/Days 0–6, 21–27, 38–44 | 40 to 42 mg/kg/inj (q.d.) | |

ASSAYS

A number of assays were performed to show the effect of combining the hemopoiesis inhibitory factor and hemopoiesis growth factor on the proliferation of hemopoietic cells during chemotherapy. The study was designed to determine whether the progenitor cell compartment of the bone marrow can be adequately protected from the cytotoxic effects of chemotherapy so that intensive therapy could be delivered and duration of the negative effects of a leukopenic nadir abbreviated without the need for marrow rescue.

Three groups of BALB/C mice were used in this study. Mice of the three groups were treated as follows (i.e., with Ara-C, the abbreviation of cytosine arabinoside, as the cytotoxic agent, AcSDKP as the hemopoiesis inhibitory factor, and GM-CSF as the hemopoiesis growth factor):
Group 1: Ara-C
Group 2: Ara-C+GM-CSF
Group 3: Ara-C+AcSDKP+GM-CSF
The animals of Group 3 were subjected to treatment according to the method of this invention. On the other hand, both Groups 1 and 2 are control groups.

Below is a detailed description of the experimental procedures outlined in Table 1:

Minipump implantations and excisions: The 200 μl capacity ALZET™ osmotic minipump Model 2001 (Alza Corporation, Palo Alto, Calif.) primed to deliver 1.0 μL/hour for 7 days was used for continuously administering the 100 ng/hour of AcSDKP in each cycle. More specifically, during each cycle, AcSDKP primed pumps were implanted s.c. prior to the first administration of Ara-C in the A.M. of day zero and excised in the A.M. of day 7. The first administration of Ara-C was in the A.M. of day zero and the last administration in the A.M. of day 6 (q.d., or once per day).

Treatment cycle: For the animals of Group 3, each cycle consists of a period in which Ara-C and AcSDKP were administered, a period in which the administered Ara-C and AcSDKP were purged, a period in which GM-CSF was administered, and, finally, a further recovery period. More specifically, after 7 consecutive days of Ara-C treatment during which time AcSDKP was administered by continuous s.c. infusion (see the preceding paragraph), a 2-day period followed so as to allow for purging of both AcSDKP and Ara-C. GM-CSF was then administered for 4 days (b.i.d., or twice per day), and the animals were permitted 4–8 more days at the end of the GM-CSF administration to recover before the initiation of the subsequent cycle (as in Cycles I and II) or before the collection of the last blood samples (as in Cycle III).

Blood sample collection: Blood samples (maximum attainable volume) for clinical pathology evaluations were collected from mice at euthanasia. The mice were food-fasted overnight prior to blood collection and samples were collected by puncture of the retro-orbital sinus after anesthetization by $CO_2$ inhalation.

Analysis of blood samples: Hematology data were collected electronically and processed by the HUMMINGBIRD™ computer system (Laboratories Consulting, Inc., Madison, Wis.). Blood samples were processed and evaluated for the parameters specified (polymorphonuclear cell, platelet, and white blood cell counts in $10^3$ cells/mm as shown in Tables 2 and 3) using a Sysmex TOAE-2500 hematology analyzer (TOA Medical Electronics, Kobe, Japan).

RESULTS

Comparison of the results from Groups 1 and 2 reveals the effect of GM-CSF on the recovery of blood cells against Ara-C. See the right-hand column "percent change," i.e., (cell count from Group 2/cell count from Group 1)×100%, in Table 2. The data in Table 2 (as well as in Table 3) are log transformed to minimize the effect of outliers and the geometric means of the data are used for the analyses. The difference in the means between two test groups are compared for each of three different stages, i.e., chemotherapy (days 0–4, 21–25 and 38–42 in Cycles I, II and III, respectively), nadir (days 5–10, 26–31 and 43–48 in Cycles I, II and III, respectively), or recovery (days 11–20, 32–37 and 49–56 in Cycles I, II and III, respectively). Significant differences are marked by a large dot, which stands for $P<0.003$, a statistically significant p-value for data compared between two groups combined over the three cycles.

Table 2 shows that only platelet counts (but not polymorphonuclear cell counts and white blood cell counts) were significantly increased (p=0.0003) during the recovery periods. However, there were no other significant responses to either the polymorphonuclear cell counts and white blood cell counts. Rather, the white blood cell counts actually decreased during the recovery period for both Cycles II and III. Thus, GM-CSF did not enhance the ability of the animals to tolerate multiple cycles of chemotherapy.

TABLE 2

| CELL | CYCLES | TIME | PERCENT CHANGE |
|---|---|---|---|
| POLYMORPHONUCLEAR CELL COUNT | CYCLE I | Chemotherapy | −0.2001 |
| | | Nadir | 23.1962 |
| | | Recovery | 21.7299 |
| | CYCLE II | Chemotherapy | 19.8969 |
| | | Nadir | 9.4827 |
| | | Recovery | −10.9401 |
| | CYCLE III | Chemotherapy | 29.7855 |
| | | Nadir | 1.6526 |
| | | Recovery | −0.7213 |
| PLATELET COUNT | CYCLE I | Chemotherapy | 30.5966 |
| | | Nadir | 0.0332 |
| | | Recovery | 10.6804● |
| | CYCLE II | Chemotherapy | 0.5878 |
| | | Nadir | 0.0259 |
| | | Recovery | 20.4577● |
| | CYCLE III | Chemotherapy | 15.5436 |
| | | Nadir | 14.0708 |
| | | Recovery | 11.9135● |
| WHITE BLOOD CELL COUNT | CYCLE I | Chemotherapy | −9.1838 |
| | | Nadir | 17.5916 |
| | | Recovery | 5.3418 |
| | CYCLE II | Chemotherapy | 43.1551 |
| | | Nadir | 40.2987 |
| | | Recovery | −7.2022 |
| | CYCLE III | Chemotherapy | 7.717 |
| | | Nadir | −9.5103 |
| | | Recovery | −0.8913 |

Comparison of the results from Groups 2 and 3, on the other hand, reveals that the presence of AcSDKP during chemotherapy contributed to subsequent enhancement of blood cell levels by GM-CSF.

As shown in Table 3, both polymorphonuclear cell counts and white blood cell counts significantly increased during the recovery periods (p=<0.0001 and p=0.0001, respectively). Such increases demonstrate that the combined use of AcSDKP, a hemopoietic cell inhibitory factor, and GMCSF, a hemopoietic cell growth factor allows multiple cycles of chemotherapy.

Figure 2:
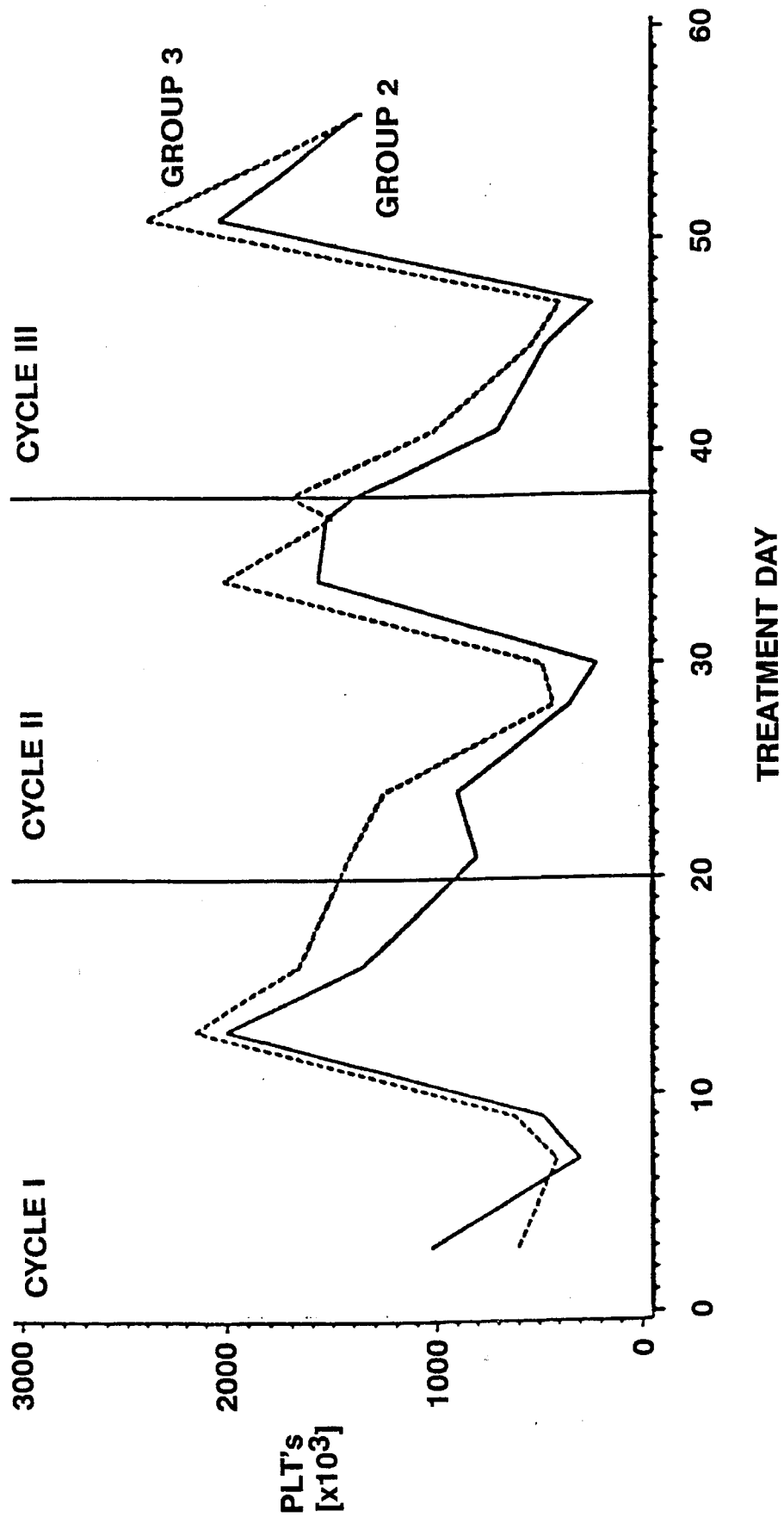
FIG. 2 is a graph showing promotion of regeneration of platelets during chemotherapy by a method which is an embodiment of this invention.
Figure 3:
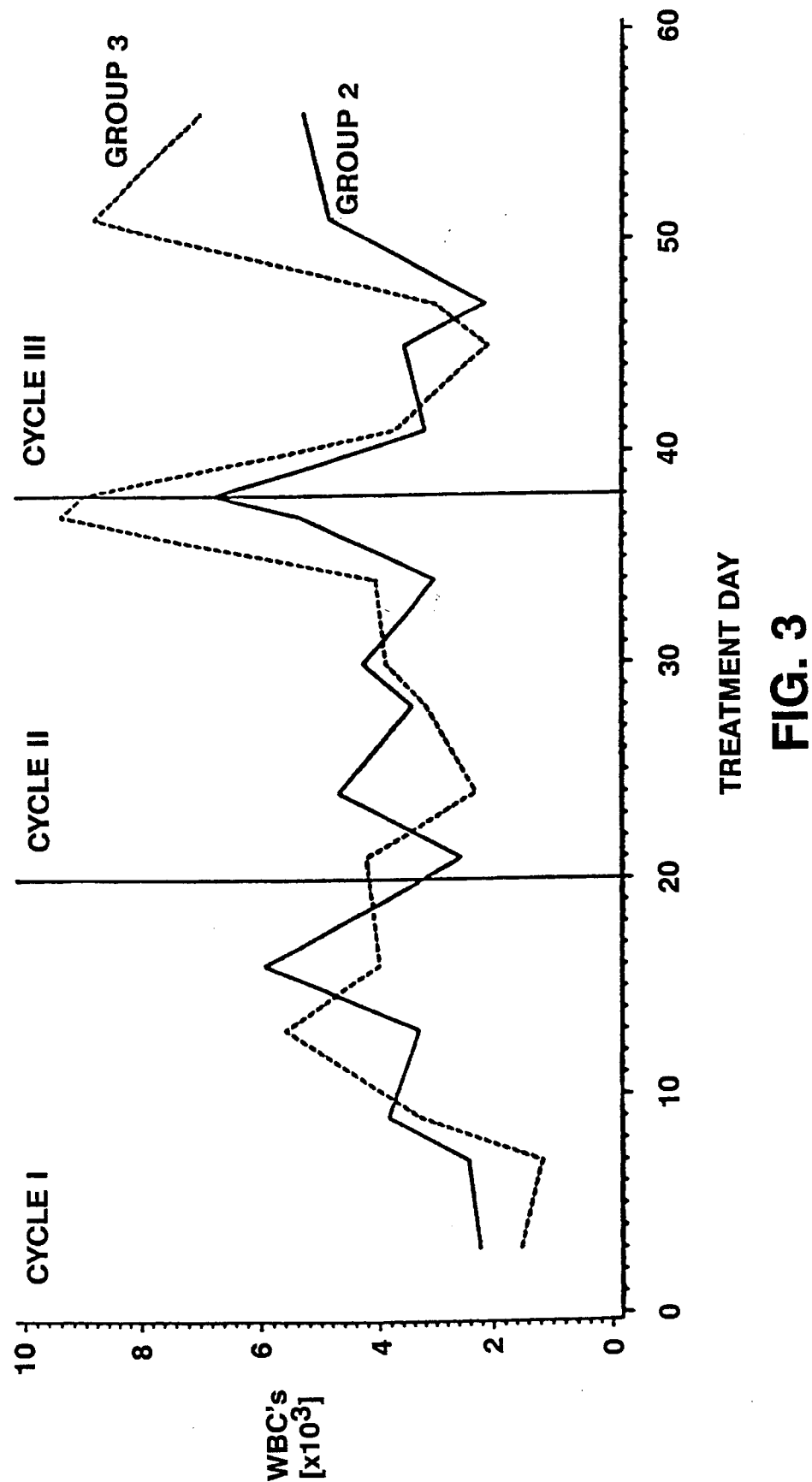
FIG. 3 is a graph showing promotion of regeneration of white blood cells during chemotherapy by a method which is an embodiment of this invention.

The results in Table 2 are reproduced in FIG. 1 (polymorphonuclear cell counts), FIG. 2 (platelet cell counts), and FIG. 3 (white blood cell counts). Note that platelet counts also significantly increased during the nadir periods (p=0.0006).

TABLE 3

| CELL | CYCLE | TIME | PERCENT CHANGE |
|---|---|---|---|
| POLYMORPHONUCLEAR CELL COUNT | CYCLE I | Chemotherapy | −66.466 |
| | | Nadir | −27.344 |
| | | Recovery | 52.314● |
| | CYCLE II | Chemotherapy | −44.682 |
| | | Nadir | 130.128 |
| | | Recovery | 100.223● |
| | CYCLE III | Chemotherapy | 37.246 |
| | | Nadir | 42.105 |
| | | Recovery | 95.829● |
| PLATELET COUNT | CYCLE I | Chemotherapy | −53.4439 |
| | | Nadir | 20.9005● |
| | | Recovery | 23.6811 |
| | CYCLE II | Chemotherapy | 29.203 |
| | | Nadir | 49.9274● |
| | | Recovery | 13.851 |
| | CYCLE III | Chemotherapy | 36.6101 |
| | | Nadir | 32.1586● |
| | | Recovery | −0.7018 |
| WHITE BLOOD CELL COUNT | CYCLE I | Chemotherapy | −39.0687 |
| | | Nadir | −47.8669 |
| | | Recovery | 29.1779● |
| | CYCLE II | Chemotherapy | −57.7294 |
| | | Nadir | −10.6607 |
| | | Recovery | 44.2989● |
| | CYCLE III | Chemotherapy | 19.207 |
| | | Nadir | −9.4556 |
| | | Recovery | 50.2142● |

OTHER EMBODIMENTS

The foregoing description has been limited to specific embodiments of this invention. It will be apparent, however, that variations and modifications may be made to the invention, with the attainment of some or all of the advantages of the invention. Such embodiments are also within the scope of the following claims.

What is claimed is:

1. A method of promoting regeneration of hemopoietic cells in a subject undergoing chemotherapy or radiotherapy, said method comprising:

administering to the subject a first amount of a hemopoiesis inhibitory factor, where said hemopoiesis inhibitory factor is AcSDKP or an agonist thereof and said first amount being effective to reduce the proliferation of hemopoietic cells during said chemotherapy or radiotherapy; and after said chemotherapy or radiotherapy, administering to the subject a second amount of a hemopoiesis growth factor, wherein said hemopoiesis growth factor is an interleukin, G-CSF, GM-CSF, or an agonist thereof and said second amount being effective to stimulate the proliferation of hemopoietic cells.

2. The method of claim 1 wherein said hemopoiesis inhibitory factor is AcSDKP (SEQ ID NO:2).

3. The method of claim 1, wherein said hemopoiesis growth factor is an interleukin.

4. The method of claim 1, wherein said hemopoiesis growth factor is IL-1, IL-3, IL-6, or IL-11; or an agonist thereof.

5. The method of claim 1, wherein said hemopoiesis growth factor is G-CSF.

6. The method of claim 1, wherein said hemopoiesis growth factor is GM-CSF.

7. The method of claim 2, wherein said hemopoiesis growth factor is GM-CSF.

8. The method of claim 2, wherein said hemopoiesis growth factor is G-CSF.

9. The method of claim 2, wherein said hemopoiesis growth factor is an interleukin.

10. The method of claim 1, wherein the subject is undergoing chemotherapy with a cytotoxic agent.

11. The method of claim 10, wherein said cytotoxic agent is cyclophosphamide, taxol, 5-fluorouracil, adriamycin, cisplatinum, methotrexate, cytosine arabinoside, mitomycin C, prednisone, vindesine, carboplatinum, or vincristine; or an agonist thereof.

12. The method of claim 11 wherein said cytotoxic agent is cytosine arabinoside.

13. The method of claim 10, wherein said cytotoxic agent is an antiviral agent.

14. The method of claim 13, wherein said antiviral agent is AZT.

15. The method of claim 12, wherein said hemopoiesis inhibitory factor is AcSDKP (SEQ ID NO:2) and said hemopoiesis growth factor is GM-CSF.

16. The method of claim 12, wherein said hemopoiesis inhibitory factor is AcSDKP (SEQ ID NO:2) and said hemopoiesis growth factor is G-CSF.

17. The method of claim 12, wherein said hemopoiesis inhibitory factor is AcSDKP (SEQ ID NO:2) and said hemopoiesis growth factor is an interleukin.

18. The method of claim 1, wherein the subject is undergoing radiotherapy.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 5 amino acids
( B ) TYPE: amino acid
( C ) STRANDEDNESS: Not Relevant
( D ) TOPOLOGY: linear ( i i ) MOLECULE TYPE: protein ( i x ) FEATURE:
( A ) NAME/KEY: Modified-site
( B ) LOCATION: 1
( D ) OTHER INFORMATION: Xaa is pyroglutamic acid.

( x i ) SEQUENCE DESCRIPTION: SEQ ID NO:1:

Xaa  Glu  Asp  Cys  Lys
1                    5

( 2 ) INFORMATION FOR SEQ ID NO:2:

( i ) SEQUENCE CHARACTERISTICS:
( A ) LENGTH: 4 amino acids
( B ) TYPE: amino acid
( C ) STRANDEDNESS: Not Relevant
( D ) TOPOLOGY: linear ( i i ) MOLECULE TYPE: protein ( i x ) FEATURE:
    ( A ) NAME/KEY: Modified-site
    ( B ) LOCATION: 1
    ( D ) OTHER INFORMATION: Xaa is a Serine whose amino
        acid functionality is substituted with an acetyl group.

( x i ) SEQUENCE DESCRIPTION: SEQ ID NO:2:

Xaa Asp Lys Pro
1